United States Patent [19]

Hedgcoth et al.

[11] Patent Number: 4,705,299

[45] Date of Patent: Nov. 10, 1987

[54] PLASTIC IDENTITY CARD CAPABLE OF PROVIDING AN INKLESS FINGERPRINT AND METHOD OF DEVELOPING INKLESS PRINTS ON PLASTIC CARD

[75] Inventors: Virgil Hedgcoth, Pomona; Douglas C. Arndt, Thousand Oaks, both of Calif.

[73] Assignee: Identicator Corp., San Bruno, Calif.

[21] Appl. No.: 867,058

[22] Filed: May 27, 1986

[51] Int. Cl.4 .......................... B42D 15/00; A61B 5/10

[52] U.S. Cl. .......................................... 283/68; 283/78; 283/904; 427/1

[58] Field of Search ...................... 283/1 A, 68, 69, 70, 283/78, 904; 428/40; 118/31.5; 427/1

[56] References Cited

U.S. PATENT DOCUMENTS

| | | | |
|---|---|---|---|
| 1,499,955 | 7/1924 | Stoddard | 283/69 |
| 2,020,376 | 11/1935 | Rich | 283/68 |
| 2,712,514 | 7/1955 | English, Jr. | 283/78 |
| 3,408,217 | 10/1968 | Obuchi | 283/68 |
| 3,412,493 | 11/1968 | French | 283/78 |
| 3,664,910 | 5/1972 | Hollie | 283/69 |
| 4,029,012 | 6/1977 | Smith et al. | 283/69 |
| 4,325,570 | 4/1982 | Estrada | 283/78 |
| 4,504,408 | 3/1985 | Morton | 283/69 |
| 4,557,964 | 12/1985 | Magmotta | 428/40 |

*Primary Examiner*—Paul A. Bell
*Assistant Examiner*—Paul M. Heyrana, Sr.
*Attorney, Agent, or Firm*—Jackson & Jones

[57] ABSTRACT

A plastic identity card is provided with an ink absorbent coating over a preassigned space thereon. The ink absorbent coating includes a chemical reagent capable of chemically reacting with a substantially colorless developer solution applied by a finger thereto to provide a perceivable colorant product representative of the fingerprint ridge pattern.

16 Claims, 3 Drawing Figures

PLASTIC IDENTITY CARD CAPABLE OF PROVIDING AN INKLESS FINGERPRINT AND METHOD OF DEVELOPING INKLESS PRINTS ON PLASTIC CARD

BACKGROUND OF THE INVENTION

1. Origin of the Invention

The present invention relates to personal plastic identity cards adapted to carry fingerprints, and, more particularly, to an article and method of providing inkless fingerprints on such cards.

2. Description of the Prior Art

Plastic identity cards which contain information identifying the card holder are in common use. Such cards normally have a nonporous surface with the identity information such as the cardholder's name, license or card number etc. either laminated into or embossed on the plastic. Such cards are often provided with a relatively porous ink receptive coating over a rectangular area, which area is designed to receive the signature of the card holder. Such ink receptive coatings are conventionally placed over the designated area by silk screening or hot stamping, have also been placed over areas designed to receive the fingerprints so that the cardholder's finger (or thumb) may be rolled in conventional fingerprint ink and then pressed onto the coating. The need for the card holder's fingerprint on the identity card is becoming increasingly important to prevent the use of such identity cards by imposters.

Conventional ink fingerprinting techniques have several well known drawbacks, such as the staining of the hands of the person being fingerprinted with the colored ink (normally black). In addition, plastic identity cards normally experience considerable handling which tends to cause conventional ink prints to smudge. Such smudging may render the print useless.

The above disadvantages of personal identity cards designed to incorporate the holders prints thereon have been overcome by the present invention.

SUMMARY OF THE INVENTION

In accordance with the present invention, a personal plastic identity card is provided with a space thereon reserved for one or more fingerpints. An ink absorbent adherent coating is disposed over said space, for example, by silk screening or hot stamping. The coating contains a chemical reagent capable of interacting with a substantially colorless developer solution placed on the coating by the card holder's finger after the card has been manufactured to provide a perceivable colorant product representative of the ridge pattern of the finger.

The method of this invention includes the steps of (1) mixing a liquid reagent with a chemical compound capable of providing an adherent ink absorbent coating on the card, (2) applying the mixture over an area on the card reserved for one or more fingerprints, (3) applying a substantially colorless liquid developer solution of a finger of the card holder and (4) pressing the finger coated with the developer over the coating, the liquid reagent and developer solution chemically interacting to provide a perceivable colorant product representative of the fingerprint ridge pattern.

The features and steps of the present invention, which are believed to be novel, are set forth in the appended claims. This invention, as to its organization and advantages, may best be understood by reference to the following description taken in conjunction with the accompanying drawings.

DESCRIPTION OF THE PREFERRED EMBODIMENT

Figure 1:
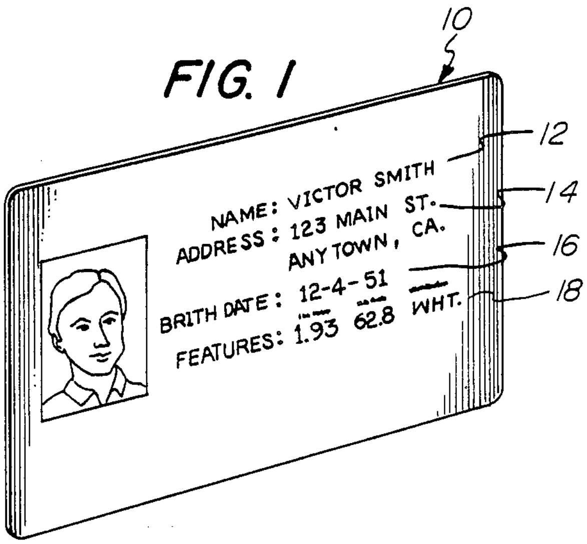
FIG. 1 is a plan view of the front of a typical personal identity card which may incorporate the features of the present invention.
Figure 2:
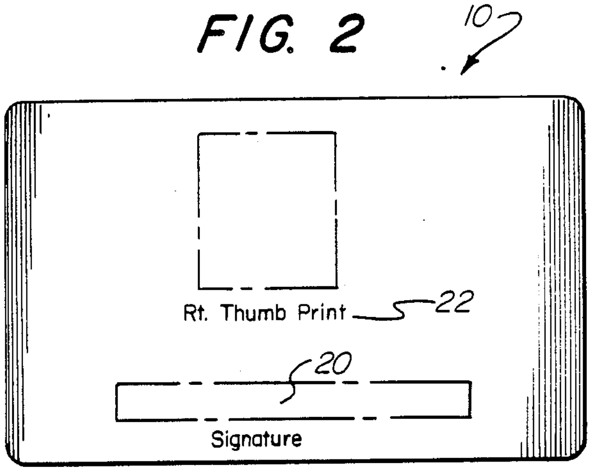
FIG. 2 is a plan view of the back of the card of FIG. 1 illustrating that spaces have been reserved for the cardholder's signature and fingerprint.
Figure 3:
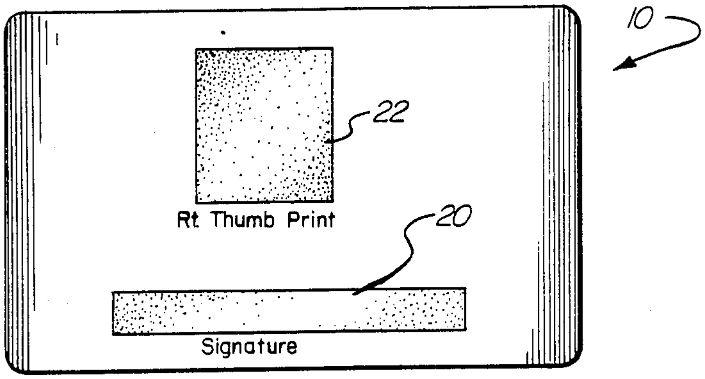
FIG. 3 is another view of the back of the card of FIG. 1 after an ink receptive coating containing a chemical fingerprinting reagent has been applied to the reserved spaces in accordance with this invention.

Referring now to the drawing and particularly to FIGS. 1 and 2 the front and back of a personal identity card 10 manufactured of a nonporous plastic such as polyvinylchloride ("PVC") or polyester is illustrated. The card 10 includes on the front thereof (FIG. 1) printed or typed personalized information such as the card holder's name, identifying code or license number, address etc. laminated into the card in areas 12–18 as illustrated. The back side of the card (shown in FIG. 2) is provided with preassigned areas 20 and 22 for receiving the signature and thumb print of the card holder, respectively.

Both the front and back surfaces of the card 10 are nonporous (to the extent they will not absorb ink or dyes) when the plastic has cured. Therefore it is necessary to bond or apply an adherent porous coating over such areas of the card which are to bear an ink signature or an ink fingerprint. Where the card is made of polyvinylchloride ("PVC") it is customary to silk screen a mixture of vinyl resin and a flatting agent such as silica over the area designed to receive the signature. This technique has also been used to provide an area designed to receive a conventional ink fingerprint. One such conventional mixture comprises vinyl resins manufactured and marketed by NAZDAR Corporation under the product numbers VF170 and VF180 (needed to bond with the PVC), a resin thinner also referred to as VF180 and Syloid 74 (silica flatting agent manufactured by the W. R. Grace Company. Many vinyl resins, thinners (e.g. keytones, napths, acetones) and flatting agents may be mixed and applied to a nonporous plastic card to provide a porous adherent coating which is ink (or dye) absorbent. Such mixtures are well known.

We have discovered that a liquid reagent solution such as that described in U.S. Pat. No. 4,029,012 (assigned to assignee of this application) may be mixed with the chemical compound used to provide the ink absorbent coating and that the resulting mixture may then be applied as by silk screening to areas designed for receiving fingerprints etc. The subsequent application of the developer solution described in the above U.S. Pat. No. 4,029,012 results in a chemical reaction between the reagent and developer which produces a colorant product in the form of a permanent record integral with the ink absorbent medium.

In accordance with the present invention, a liquid reagent such as that described in the '012 patent is mixed with a chemical compound capable of adhering to the plastic card and providing an ink absorbent coating thereon. The mixture of reagent and chemical compound is then applied, for example, by silk screening over the space 22 (and over the space 20 if desired) of the card 10. The mixture is allowed to dry. The liquid reagent is capable of chemically reactng with a substantially colorless developer solution such as that described in U.S. Pat. No. 4,029,012 when impressed on the preassigned space by a finger and providing a perceivable colorant product representative of a fingerprint ridge pattern.

As pointed out in U.S. Pat. No. 4,029,012 the reagent solution can include as the active ingredient 8-hydroxyquinoline derivatives where X and Y can be any of the following group on the basic structure:

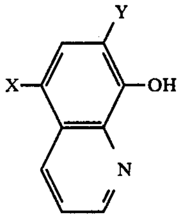

| X | Y |
|---|---|
| H | H |
| $SO_2H$ | $SO_2H$ |
| $SO_2H$ | H |
| H | $SO_2H$ |
| $SO_2H$ | I |
| $SO_2H$ | Br |
| $SO_2H$ | Cl |
| Br | Br |
| Br | $SO_2H$ |
| Cl | Cl |
| I | I |
| $SO_2H$ | $NO_2$ |
| $NO_2$ | $SO_2H$ |

Preferably the reagent is propyl gallate or a salt of 8-quinolinol, dimethyldithiocarbamic acid sodium salt dihydrate, sodium ferrocyanide, sodium nitrate, potassium thiocyanate or 8-hydroxyquinoline sulfate. The above reagents chemically react with a suitable liquid developer solution containing a metallic salt such as ferric chloride to produce a change in color of the medium or ink absorbent coating e.g. black on a white background. Other examples of salts of metals and transition metals for use in the developer solution may be found in U.S. Pat. No. 4,029,012.

We have found that one-quarter (¼) ounces by weight of propyl gallate mixed with one fluid ounce of the chemical compound (i.e. NASDAR VF 180 thinner, VF180 resin, VR170 resin and Syloid 74) conventionally used to provide the ink receptive coating, will provide good results. To develop a fingerprint on the coating, it is simply necessary to roll the cardholder's finger (or thumb) across a pad containing ferric chloride and then press (or roll) the finger onto the card area containing the coating. A high construst dark print (representing the ridge pattern) on a white background results. The print is exceptionally durable and long lasting. However, if desired, a thin film laminate or overlay of a clear permanent coating (e.g. an acetate) may be applied over the paint to afford additional protection.

A pen containing the developer solution may be used to place the cardholder's signature on the signature space 20 (where the reagent has also been applied to such space) to provide a permanent signature.

The ink coating of reagent and ink absorbent compound may also be applied by mixing the reagent with polyester or other vinyl resin and binding the mixture to a sheet of metalized mylar. The particle carrying mylar sheet is then affixed to the spaces 20 and/or 22 of the card 10 by pressure and heat. The mylar strip is then removed leaving a deposit of polyester and reagent on the spaces 22 and/or 20.

In an alternative embodiment the space 22 (and 20) may be coated with a very thin metallic film such as aluminum, brass, copper or stainless steel, (e.g. by a hot stamping process) so that the developer solution, ferric chloride, when impressed on the film by the cardholder's finger will etch away the metal film in a pattern corresponding to the ridge pattern. For example when a black mylar is used as the backing material for the metal film the resulting ridge pattern will show up as a dark color against a contrasting background.

The above description presents the best mode contemplated in carrying out our invention. Our invention is, however, susceptible to modifications and alternate constructions from the embodiments shown in the drawings and described above. Consequently, it is not the intention to be limited to the particular embodiments disclosed. On the contrary, the invention is intended and shall cover all modifications, sizes and alternate constructions falling within the spirit and scope of the invention, as expressed in the appended claims when read in light of the description and drawing.

What is claimed is:

1. In a method of developing inkless fingerprints on a nonporous plastic identity card the steps of:

mixing a liquid reagent with a chemical compound capable of providing an adherent ink absorbent coating on the plastic card;

applying the mixture of reagent and chemical compound over or section of the card of sufficient size to receive a fingerprint to provide a porous ink receptive coating over said section;

applying a substantially colorless liquid developer solution to a finger of a person whose print is desired on the card; and pressing the finger with developer solution thereon over the porous coating, the liquid reagent and developer solution chemically interacting to provide a perceivable colorant product representative of the fingerprint ridge pattern.

2. The method of claim 1 wherein the chemical compound comprises vinyl resins and a flatting agent.

3. The method of claim 2 wherein the flatting agent is silica.

4. The method of claim 3 wherein the mixture is applied to the card by silk screening.

5. The method of claim 1 wherein the chemical composition is a polyester material and, wherein the mixture is first secured to a mylar backing and the mylar backed mixture is then applied to the card by heat and pressure to permanently bind the mixture to the card.

6. The method of claim 4 wherein the chemical compound comprises vinyl resins, and a vinyl resin thinner and the liquid reagent includes one of the salts of 8-quinolinol, dimethyldithiocarbamic acid sodium salt dihydrate, sodium ferrocyanide, sodium nitrate, potassium thiocyanate or 8-hydroxyquinoline sulfate and propyl gallate.

7. The method of claim 5 wherein the liquid reagent includes one of the salts of 8-quinolinol, dimethyldithiocarbamic acid sodium salt dihydrate, sodium ferrocyanide, sodium nitrate, potassium thiocyanate or 8-hydroxyquinoline sulfate and propyl gallate.

8. A method of manufacturing a plastic identity card capable of developing an inkless fingerprint comprising:

(a) providing a substantially non absorbent plastic identity card having preassigned space thereon for receiving a fingerprint of the person identified by the card;

(b) mixing a liquid reagent with a chemical compound capable of adhering to the plastic card and providing an ink absorbent coating thereon;

(c) applying the mixture of reagent and chemical compound over the preassigned space on the card; and (d) allowing the mixture to dry, the liquid reagent being capable of chemically reacting with a substantially colorless developer solution when impressed on the preassigned space by a finger and providing a perceivable colorant product representative of a fingerprint ridge pattern.

9. The method of claim 8 wherein the reagent and developer are water soluble inorganic compounds which react to form a non soluble colorant precipitate.

10. The method of claim 9 wherein the chemical compound includes vinyl resins for bonding to the plastic and a flatting agent.

11. The method of claim 10 wherein the applying step comprises silk screening the mixture onto the preassigned area of the card.

12. The method of claim 11 wherein the reagent is propyl gallate.

13. The method of claim 12 wherein the reagent is a salt of the group consisting of 8-quinolinol, dimethyldithiocarbamic acid sodium salt dihydrate, sodium ferrocyanide, sodium nitrite, potassium thiocyanate, and 8-hydroxyquinoline sulfate.

14. A plastic identity card capable of providing an inkless fingerprint comprising:

(1) a plastic identity card having a space thereon reserved for one or more fingerprints; and (2) an ink absorbent coating disposed over said fingerprint space, said coating containing an intergal mixture of a reagent capable of chemically interacting with a developer solution placed on the coating by a person's finger to provide a perceivable colorant product representative of the ridge pattern of the person's finger.

15. In a method of developing inkless fingerprints on a nonporous plastic identity card the steps of:

depositing a thin metal film over a section of the card of sufficient size to receive a fingerprint the metal film providing a light reflective contrast with underlying layer;

applying a liquid developer solution to a finger of a person whose fingerprint is desired on the card, and pressing the finger with the developer solution thereon over the metallic film the developer solution chemically reacting with the metallic film to etch away the metal in contact with the developer solution and expose the underlying surface whereby the contrast between the unetched and etched portion of the metallic layer represents a fingerprint ridge pattern.

16. The method of claim 15 wherein the metallic film is deposited on the card by initially applying the metallic film to a mylar backing material and then laminating the mylar with the metallic film thereon to the card so that the metallic film is exposed.

* * * * *